(12) United States Patent
Ward et al.

(10) Patent No.: US 6,673,965 B1
(45) Date of Patent: Jan. 6, 2004

(54) HYDROXAMIC ACID DERIVATIVE AS INHIBITOR OF THE FORMATION OF SOLUBLE HUMAN CD23

(75) Inventors: John Gerard Ward, Harlow (GB); Andrew Faller, Harlow (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 10/111,209

(22) PCT Filed: Oct. 25, 2000

(86) PCT No.: PCT/EP00/10649

§ 371 (c)(1),
(2), (4) Date: Jul. 16, 2002

(87) PCT Pub. No.: WO01/30747

PCT Pub. Date: May 3, 2001

(30) Foreign Application Priority Data

Oct. 27, 1999 (GB) ............................................. 9925470

(51) Int. Cl.$^7$ ............................................. C07C 259/04
(52) U.S. Cl. ........................ 562/621; 514/417; 514/459; 514/221
(58) Field of Search .................... 562/621; 514/459, 514/417, 221

(56) References Cited

FOREIGN PATENT DOCUMENTS

| WO | WO9702239 A | 1/1997 |
|---|---|---|
| WO | WO 9967201 A | * 12/1999 |
| WO | WO. 99/67201 | * 12/1999 |

* cited by examiner

Primary Examiner—Alan L. Rotman
Assistant Examiner—Héctor M Reyes
(74) Attorney, Agent, or Firm—Soma G. Simon; Mary E. McCarthy; Charles M. Kinzig

(57) ABSTRACT

A compound of formula (I)

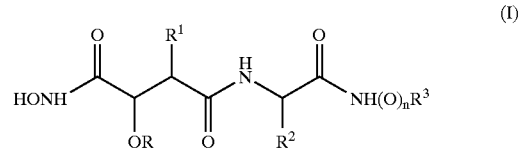

wherein:

R isopropyl;

n is 0;

$R^1$ is naphthylmethyl;

$R^2$ is t-butyl; and $R^3$ is methyl;

is useful in the treatment of disorders mediated by s-CD23.

8 Claims, No Drawings

HYDROXAMIC ACID DERIVATIVE AS INHIBITOR OF THE FORMATION OF SOLUBLE HUMAN CD23

This invention relates to a novel inhibitor of the formation of soluble human CD23 and its use in the treatment of conditions associated with excess production of soluble CD23 (s-CD23) such as autoimmune disease, inflammation and allergy. CD23 (the low affinity IgE receptor FceRII, Blast 2), is a 45 kDa type II integral protein expressed on the surface of a variety of mature cells, including B and T lymphocytes, macrophages, natural killer cells, Langerhans cells, monocytes and platelets (Delespesse et al, *Adv Immunol*, 49 [1991] 149–191). There is also a CD23-like molecule on eosinophils (Grangette et al, *J Immunol*, 143 [1989] 3580–3588). CD23 has been implicated in the regulation of the immune response (Delespesse et al, *Immunol Rev*, 125 [1992] 77–97). Human CD23 exists as two differentially regulated isoforms, a and b, which differ only in the amino acids at the intracellular N-terminus (Yokota et al, *Cell*, 55 [1988] 611–618). In man the constitutive a isoform is found only on B-lymphocytes, whereas type b, inducible by IL4, is found on all cells capable of expressing CD23.

Intact, cell bound CD23 (i-CD23) is known to undergo cleavage from the cell surface leading to the formation of a number of welldefined soluble fragments (s-CD23), which are produced as a result of a complex sequence of proteolytic events, the mechanism of which is still poorly understood (Bourget et al *J Biol Chem*, 269 [1994] 6927–6930). Although not yet proven, it is postulated that the major soluble fragments (Mr 37, 33, 29 and 25 kDa) of these proteolytic events, all of which retain the C-terminal lectin domain common to i-CD23, occur sequentially via initial formation of the 37 kDa fragment (Letellier et al, *J Exp Med*, 172 [1990] 693–700). An alternative intracellular cleavage pathway leads to a stable 16 kDa fragment differing in the C-terminal domain from i-CD23 (Grenier-Brosette et al, *Eur J Immunol*, 22 [1992] 1573–1577).

Several activities have been ascribed to membrane bound i-CD23 in humans, all of which have been shown to play a role in IgE regulation. Particular activities include: a) antigen presentation, b) IgE mediated eosinophil cytotoxicity, c) B cell homing to germinal centres of lymph nodes and spleen, and d) downregulation of IgE synthesis (Delespesse et al, *Adv Immunol*, 49, [1991] 149–191). The three higher molecular weight soluble CD23 fragments (Mr 37, 33 and 29 kDa) have multifunctional cytokine properties which appear to play a major role in IgE production. Thus, the excessive formation of s-CD23 has been implicated in the overproduction of IgE, the hallmark of allergic diseases such as extrinsic asthma, rhinitis, allergic conjuctivitis, eczema, atopic dermatitis and anaphylaxis (Sutton and Gould, *Nature*, 366, [1993] 421–428). Other biological activities attributed to s-CD23 include the stimulation of B cell growth and the induction of the release of mediators from monocytes. Thus, elevated levels of s-CD23 have been observed in the serum of patients having B-chronic lymphocytic leukaemia (Sarfati et al, *Blood*, 71 [1988] 94–98) and in the synovial fluids of patients with rheumatoid arthritis (Chomarat et al, *Arthritis and Rheumatism*, 36 [1993] 234–242). That there is a role for CD23 in inflammation is suggested by a number of sources. First, sCD23 has been reported to bind to extracellular receptors which when activated are involved in cell-mediated events of inflammation. Thus, sCD23 is reported to directly activate monocyte TNF, IL-1, and IL-6 release (Armant et al, vol 180, J.Exp. Med., 1005–1011 (1994)). CD23 has been reported to interact with the B2-integrin adhesion molecules, CD11b and CD11c on monocyte/macrophage (S. Lecoanet-Henchoz et al, Immnunity, vol 3; 119–125 (1995)) which trigger $NO_2$-, hydrogen peroxide and cytokine (IL-1, IL-6, and TNF) release. Finally, IL-4 or IFN induce the expression of CD23 and its release as sCD23 by human monocytes. Ligation of the membrane bound CD23 receptor with IgE/anti-IgE immune complexes or anti CD23 mAb activates cAMP and IL-6 production and thromboxane B2 formation, demonstrating a receptor-mediated role of CD23 in inflammation.

Because of these various properties of CD23, compounds which inhibit the formation of s-CD23 should have twofold actions of a) enhancing negative feedback inhibition of IgE synthesis by maintaining levels of i-CD23 on the surface of B cells, and b) inhibiting the immunostimulatory cytokine activities of higher molecular weight soluble fragments (Mr 37, 33 and 29 kDa) of s-CD23. In addition, inhibition of CD23 cleavage should mitigate sCD23-induced monocyte activation and mediator formation, thereby reducing the inflammatory response.

International Patent Application No. WO 96/02240 (Smithkline Beecham plc) discloses that compounds which inhibit the action of matrix metalloproteases (eg collagenase, stromelysin and gelatinase) are effective inhibitors of the release of human soluble CD23 transfected into mammalian cell culture systems.

International Patent Application No. WO 97/02239 (British Biotech Pharmaceuticals Limited) discloses that certain compounds of formula (A) have matrix metalloprotease activity:

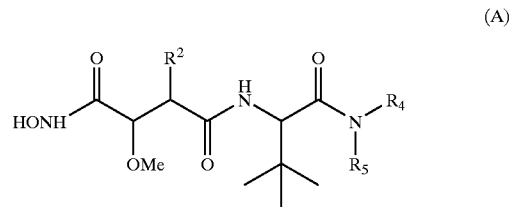

(A)

International Patent Application No. WO 99/67201 (Smithkline Beecham plc) discloses that certain compounds of formula (I) are effective inhibitors of the release of human soluble CD23 transfected into mammalian cell culture systems:

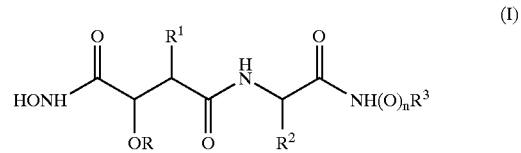

(I)

It has now been surprisingly found that certain compounds of formula (I) have unexpectedly good bioavailability.

Accordingly, the present invention provides a compound of formula (I) above, wherein:

n is 0;
R is isopropyl;
$R^1$ is naphthylmethyl;
$R^2$ is t-butyl; and
$R^3$ is methyl.

According to a further aspect, the present invention provides the use of the compound of the invention for the production of a medicament for the treatment or prophylaxis of disorders such as allergy, inflammatory disorders and autoimmune disease in which the overproduction of s-CD23 is implicated.

In a further aspect the invention provides a method for the treatment or prophylaxis of disorders such as allergy, inflammatory disorders and autoimmune disease in which the overproduction of s-CD23 is implicated, which method comprises the administration of the compound of the invention, to a human or non-human mammal in need thereof.

The invention also provides a pharmaceutical composition for the treatment or prophylaxis of disorders such as allergy, inflammatory disorders and autoiimmune disease in which the overproduction of s-CD23 is implicated which comprises the compound of the invention and optionally a pharmaceutically acceptable carrier therefor.

Particular inflammatory disorders include CNS disorders such as Alzheimers disease, multiple sclerosis, and multi-infarct dementia, as well as the inflammation mediated sequelae of stroke and head trauma.

It is to be understood that the pharmaceutically acceptable salts, solvates and other pharmaceutically acceptable derivatives of the compound of the invention are also included in the present invention.

Salts of compounds of formula (I) include for example acid addition salts derived from inorganic or organic acids, such as hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartarates and benzoates.

Salts may also be formed with bases. Such salts include salts derived from inorganic or organic bases, for example alkali metal salts such as sodium or potassium salts, and organic amine salts such as morpholine, piperidine, dimethylamine or diethylamine salts.

It has surprisingly been found that the compound of the present invention exhibits advantageous in-vivo absorption properties via the oral route as well as being a potent and selective inhibitor of CD23 processing.

The compound of the invention may be prepared by use of any appropriate conventional method, for example by analogy with the methods disclosed in patent publication WO 97/02239 (British Biotech Pharmaceuticals Limited).

Accordingly, a further aspect of the invention provides a process for preparing the compound of the invention as defined hereinabove, which process comprises:

(a) deprotecting a compound of formula (II):

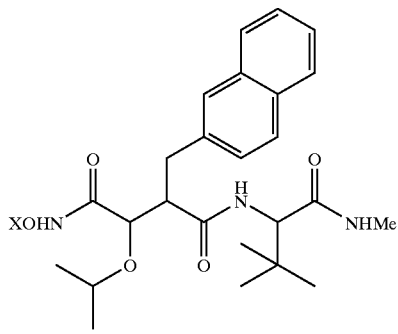

(II)

wherein X is a protecting group such as benzyl or trimethylsilyl or (b) reacting a compound of formula (III):

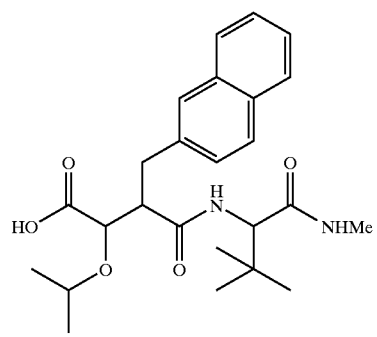

(III)

wherein the hydroxy is optionally protected, with hydroxylaine or a salt thereof.

Compounds of formulae (II) and (III) are novel and form a further aspect of the invention.

The compound of formnula (II) can be prepared from the compound of formula (III) by reaction with a protected hydroxylamnine. The compound of formula (III) having one protected hydroxy groupi can be converted by hydrolysis to the unprotected compound of formula (III).

Suitable protecting groups for a hydroxamic acid are well known in the art and include benzyl, trimethylsilyl, t-butyl and t-butyldimethylsilyl.

Suitable protecting groups for a carboxylic acid are well known in the art and include t-butyl, benzyl and methyl.

The compound of formula (III) can be prepared by reacting a compound of formula (IV) or (IVa):

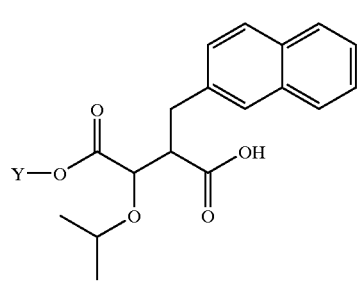

(IV)

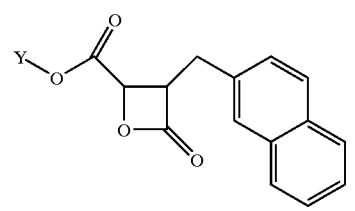

(IVa)

wherein Y is a protecting group for carboxyl, with a compound of formula (V):

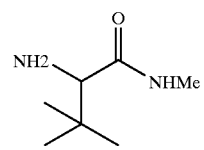

(V)

If (IVa) is used a subsequent alkylation of the hydroxyl group may then be required.

The compound of formula (IV) can be prepared by protecting a corresponding compound in which Y is hydrogen, which in turn can be prepared by:

(a) reacting a compound of formula (VI):

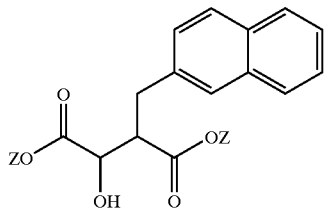

(VI)

wherein $R^1$ is as defined hereinabove and Z is a protecting group for carboxyl, with an alkylating agent; and (b) removing the protecting groups.

The compound of formula (VI) wherein Z is hydrogen can be prepared by reacting a diester (such as the dimethyl or diethyl ester) of 2-hydroxy succinic acid with a compound of formula $R^1X'$ in the presence of a strong base such as lithium diisopropylamide, wherein $R^1$ is naphthylmethyl X' is a leaving group such as bromine or iodine, and then hydrolysing the resulting compound to remove the ester groups.

The isomers, including stereoisomers, of the compound of the present invention may be prepared as mixtures of such isomers or as individual isomers. The individual isomers may be prepared by any appropriate method, for example individual stereoisomers may be prepared by stereospecific chemical synthesis starting from chiral substrates or by separating mixtures of diastereoisomers using known methods. In a preferred aspect, the invention provides compounds of formula (IA):

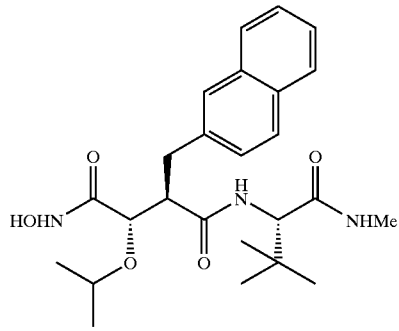

(IA)

It is preferred that the compounds are isolated in substantially pure form.

As stated herein an inhibitor of the formation of soluble human CD23 has useful medical properties. Preferably the active compounds are administered as pharmaceutically acceptable compositions.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, taagacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthrnatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg/ml of compound but more generally 0.1 to 10 mg/ml. for use with standard nebulisation equipment.

An effective amount will depend on the relative efficacy of the compounds of the present invention, the severity of the disorder being treated and the weight of the sufferer. Suitably, a unit dose form of a composition of the invention may contain from 0.1 to 1000 mg of a compound of the invention (0.001 to 10 mg via inhalation) and more usually from 1 to 500 mg, for example 1 to 25 or 5 to 500 mg. Such compositions may be administered from 1 to 6 times a day, more usually from 2 to 4 times a day, in a manner such that the daily dose is from 1 mg to 1 g for a 70 kg human adult and more particularly from 5 to 500 mg. That is in the range of about $1.4 \times 10^{-2}$ mg/kg/day to 14 mg/kg/day and more particularly in the range of about $7 \times 10^{-2}$ mg/kg/day to 7 mg/kg/day.

The following example illustrates the invention but does not limit it in any way.

BIOLOGICAL TEST METHODS

Procedure 1: The ability of test compounds to inhibit the release of soluble CD23 was investigated by use of the following procedure.

RPMI 8866 Cell Membrane CD23 Cleavage Activity Assay

Plasma membranes from RPMI 8866 cells, a human Epstein-Barr virus transformed B-cell line (Sarfati et al., Immunology 60 [1987] 539–547) expressing high levels of CD23 are purified using an aqueous extraction method. Cells resuspended in homogenization buffer (20 mM HEPES pH 7.4, 150 mM NaCl, 1.5 mM MgCl2, 1 mM DTT) are broken by $N_2$ cavitation in a Parr bomb and the plasma membrane fraction mixed with other membranes is recovered by centrifugation at 10,000×g. The light pellet is resuspended in 0.2 M potassium phosphate, pH 7.2 using 2 ml per 1–3 g wet cells and the nuclear pellet is discarded. The membranes are further fractionated by partitioning between Dextran 500 (6.4% w/w) and polyethylene glycol (PEG) 5000 (6.4% w/w) (ref), at 0.25 M sucrose in a total of 16 g per 10–15 mg membrane proteins [Morre and Morre, BioTechniques 7,946–957 (1989)]. The phases are separated by brief centrifugation at 1000×g and the PEG (upper) phase is collected, diluted 3–5 fold with 20 mM potassium phosphate buffer pH 7.4, and centrifuged at 100,000×g to recover membranes in that phase. The pellet is resuspended in phosphate-buffered saline and consists of 3–4 fold enriched plasma membranes as well as some other cell membranes (e.g. lysosomes, Golgi). The membranes are aliquoted and stored at −80° C. Fractionation at 6.6% Dextran/PEG yields plasma membranes enriched 10-fold.

The fractionated membranes are incubated at 37° C. for times up to 4 hrs to produce fragments of CD23 which are separated from the membrane by filtration in 0.2 micron Durapore filter plates (Millipore) after quenching the assay with 5 uM Preparation 1 from P 30994. sCD23 released from the membrane is determined using the EIA kit from The Binding Site (Birmingham, UK) or a similar one utilizing MHM6 anti-CD23 mAb [Rowe et al., Int. J. Cancer, 29, 373–382 (1982)] or another anti-CD23 nAb as the capture antibody in a sandwich EIA. The amount of soluble CD23 made by 0.5 ug membrane protein in a total volume of 50 ul phosphate-buffered saline is measured by EIA and compared to the amount made in the presence of various concentrations of inhibitors. Inhibitors are prepared in solutions of water or dimethylsulfoxide (DMSO) and the final DMSO concentration is not more than 2%. IC50's are determined by curve fitting as the concentration where 50% inhibition of production of sCD23 is observed relative to the difference in sCD23 between controls incubated without inhibitor.

Results

N'-[4-(N-hydroxyamino)-3S-isopropoxy-2R-(2-naphthylmethyl)succinyl]-S-tert-leucine methylamide gave an IC50 of 60 nm in the above assay.

Procedure 2: The ability of test compounds to inhibit collagenase was investigated using the following procedure.

Collagenase Inhibition Assay

The potency of compounds to act as inhibitors of collagenase was determined by the method of Cawston and Barrett (Anal. Biochem. 99, 340–345, 1979), hereby incorporated by reference, whereby a 1 mM solution of the inhibitor being tested or dilutions thereof, was incubated at 37° C. for 18 h with collagen and human recombinant collagenase, from synovial fibroblasts cloned, expressed and purified from *E. Coli*, (buffered with 150 mM Tris, pH 7.6, containing 15 mM calcium chloride, 0.05% Brij 35, 200 mM sodium chloride and 0.02% sodium azide). The collagen was acetylated $^3$H type 1 bovine collagen prepared by the method of Cawston and Murphy (methods in Enzymology 80, 711,1981) The samples were centrifuged to sediment undigested collagen and an aliquot of the radioactive supernatant removed for assay on a scintillation counter as a measure of hydrolysis. The collagenase activity in the presence of 1 mM inhibitor, or dilution thereof, was compared to activity in a control devoid of inhibitor and the results reported as that concentration effecting 50% of the collagenase ($IC_{50}$).

Procedure 3: The ability of test compounds to inhibit TNF release was investigated using the following procedure.

Assay for Inhibition of Release of TNFα From Human Monocytes Stimulated by Lipopolysaccharide (LPS) Endotoxin Human monocytes, cultured in RPMI 1640 medium supplemented with 10% fetal calf serum, are centrifuged at 1000×g for 5 min and then resuspended in medium at $2 \times 10^6$ cells/ml. The cell suspension is aliquoted in 24 well plates, 1 ml per well. Compounds to be tested are dissolved in neat dimethyl sulfoxide (DMSO) and added to culture with the final DMSO concentration at 0.1%. Compounds are added to cells in triplicate wells. TNF α release is stimulated by addition of LPS to the cells at a final concentration of 200 ng/ml. Appropriate control cultures are set up in triplicates also. The plates are incubated for 18–20 hrs at 37° C., 5% $CO_2$, then centrifuged at 1000×g for 5 min. A specific ELISA for human TNFα (SmithKline Beecham) is used to measure TNF levels in the cell-free culture supernatants.

Results

N'-[4-(N-hydroxyamino)-3S-isopropoxy-2R-(2-naphthylmethyl)succinyl]-S-tert-leucine methylamide showed no effect on TNF release at 10 uM.

Procedure 4: The bioavailability of test compounds was investigated using the following bio-equivalence studies.

A Study to Estimate the i.v. Pharmacokinetic Parameters and Oral Bioavailability in Male Sprague Dawley Rat This study was carried out using a crossover design on four separate study days. Three rats received surgically-implanted femoral vein catheters for infusion of test molecules at least three days prior to the start of the study. All doses in this study were prepared using crystalline test compound.

On study day one, the animals (fed) received test compound as a 30-min intravenous infusion at a target dosage of 4.0 umol/kg (4.0 mL/kg). The dose solution was prepared in 20% aqueous Encapsin® (pH=8.0) and contained 1% DMSO. Encapsin® (Cerestar USA Inc., Hammond, Ind.) is hydroxypropyl-beta-cyclodextrin, a cyclic oligosaccharide used to enhance solubility of compounds that otherwise would require formulation using non-aqueous solvents.

On study day two, the animals (fasted) received test compound as a solution at a target dosage of 8 umol/kg by oral gavage (16 mL/kg). The dose solution was prepared in 5% aqueous succinated porcine gelatin (pH=7.5) and contained 1% DMSO. Blood samples were collected from a lateral tail vein. A 25-uL aliquot of each whole blood sample was added to 25 uL of water and allowed to stand on ice for approximately 5 min to facilitate complete hemolysis; samples then were stored frozen until analysis. Blood concentrations of test compound were quantified by LC/MS/MS (LLQ=10.0 ng/mL). Both noncompartmental and compartmental pharmacokinetic analyses were performed on these data using WinNonlin to recover the appropriate i.v. pharmacokinetic parameters. Various compartmental models and weighting paradigms were employed; a two-compartment model with first-order elimination from the central compartment and iterative least squares weighting with a weight of $1/Y^2$ provided the best fit to the observed data, according to standard model selection criteria (i.e., Akaike's Information Criterion, Schwartz Criterion, and sum of squared residuals). Pharmacokinetic parameters were calculated using the best-fit compartmental model; all calculations that required the use of AUC values (including bioavailability) were performed using the AUC recovered from noncompartmental analysis.

A Study to Estimate the i.v. Pharmacokinetic Parameters and Oral Bioavailability in Male Beagle Dogs This study was conducted using a crossover design on two separate study days, seven days apart. Three male Beagle dogs were used in this study. On each study day, a catheter was temporarily placed in a cephalic vein for blood sampling; on study day one only, a catheter was also temporarily placed in a saphenous vein for i.v. infusion.

On study day one, each animal received test compound (2.0 umol/kg target dose) as a 1-h intravenous infusion (4.0 mL/kg). The dose solution was prepared in 20% aqueous Encapsin® (pH=8.0) and contained 1% DMSO. Encapsin® (Cerestar USA Inc., Hammond, Ind.) is hydroxypropyl-beta-cyclodextrin, a cyclic oligosaccharide (7 glucose units) used to enhance solubility in the preparation of dose solutions that otherwise would require formulation using non-aqueous solvents.

On study day two, each animal received test compound (6.0 umol/kg target dose) by oral gavage (8.0 mL/kg). The dose solution was prepared in 5% aqueous succinated porcine gelatin (pH=7.5) and contained 1% DMSO.

Plasma concentrations of test compound were quantified by LC/MSIMS (LLQ=10 ng/mL). Noncompartmental methods were used for analysis of plasma concentration versus time data.

A Study to Estimate the i.v. Pharmacokinetic Parameters and Oral Bioavailability in Male Cynomolgus Monkeys This study was conducted using a crossover design on two separate study days, seven days apart. Three male Cynomolgus monkeys were used for this study. On both study days, a catheter was placed in a saphenous vein for collection of blood samples. On study day one, a catheter also was temporarily placed in a contralateral saphenous vein for i.v. infusion.

On study day one, each animal (fasted) received test compound (2.0 umol/kg target dose) as a 1-h intravenous infusion (4.0 mL/kg). The dose solution was prepared in 20% aqueous Encapsin® (pH=8.0) and contained 1% DMSO. Encapsin® (Cerestar USA Inc., Hammond, Ind.) is hydroxypropyl-beta-cyclodextrin, a cyclic oligosaccharide (7 glucose units) used to enhance solubility in the preparation of dose solutions that otherwise would require formulation using non-aqueous solvents.

On study day two, each animal (fasted) received test compound (6.0 umol/kg target dose) by oral gavage (8.0 mL/kg). The dose solution was prepared in 5% aqueous succinated porcine gelatin (pH=8.0) and contained 1% DMSO.

Blood samples were obtained from the femoral vein catheter; plasma was isolated by centrifugation. Plasma concentrations of test compound were quantified by LC/MS/MS (LLQ=10 ng/mL). Noncompartmental methods were used for pharmacokinetic analysis of plasma concentration versus time data.

Results

The results for N'-[4-(N-hydroxyamino)-3S-isopropoxy-2R-(2-naphthylmethyl)succinyl]-S-tert-leucine methylamide are compared with those for N'-[4-(N-Hydroxyamino)-3S-5 propoxy-2R-(2-naphthylmethyl)succinyl]-S-tert-leucine methoxyamide (disclosed in WO 99/67201 (SmithKline Beecham).

| | | | | |
|---|---|---|---|---|
| Structure IC50 (Parent MW) [cLogP] | 0.04 (457.57) [2.596] | | | (473.57) [4.659] (Compartmental Analysis) |
| Study | Rat | Dog | Monkey | Monkey |
| $C_{max}$ (ng/mL) | 1335 ± 296 i.v. dose = 2.0 mg/kg | 1414 ± 465 iv dose = 0.96 mg/kg | 1011 ± 175 iv dose = 0.92 mg/kg | 1359 ± 464 iv dose = 0.99 mg/kg |
| $T_{1/2}$ (min) (MRT) | 10.8 ± 5.3 (α) 234 ± 139 (β) (128 ± 77) | 252, 259, 49[b] (64.4 ± 39.7) | 691, 85.1, 208[b] (311, 59.5, 68.1[b]) | 5.32 ± 1.14 (α) 311 ± 106 (β) (115 ± 62) |
| CL (mL/min/kg) | 26.4 ± 8.5 | 10.6 ± 4.5 | 14.7 ± 3.6 | 10.4 ± 3.7 |
| $Vd_{ss}$ (L/kg) | 3.25 ± 1.70 | 0.563 ± 0.204 | 4.09, 1.11, 0.827[b] | 1.16 ± 0.57 |
| Oral F[a] (%) | 50.6 ± 10.6 (3.7 mg/kg solution) | 29.0 ± 3.7 po dose = 2.7 mg/kg | 21.1, 6.0, 22.5[b] (2.8 mg/kg Solution) | 1.4, 6.0, 1.9[b] po dose = 2.8 mg/kg |

Abbreviations:
$C_{max}$ - Maximum concentration attained after i.v. infusion;
$T_{1/2}$ - half-life,
MRT - mean residence time of test molecule;
CL - systemic plasma clearance;
$VD_{ss}$ - steady-state volume of distribution;
F - percent bioavailability
[a]Bioavailability was calculated by dividing the does-normalized $AUC_{0-t}$ (where t is the last time point with observable test compound concentrations from the oral segment (in the case of rate study) or measurable drug concentrations in oral or intraduodenal leg of study (dog and monkey studies)) by the dose-normalized $AUC_{0-t}$ from the i.v. segment and multiplying by 100.
[b]Individual values listed due to large variability; animals always listed in the same order.

Preparation a) 3S-t-Butoxycarbonyl-2R-(2-naphthylmethyl) propiolactone

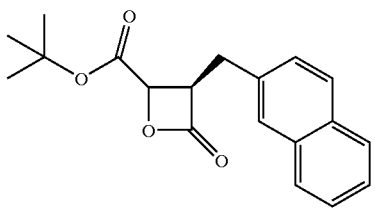

(t-Butyl-(3R)-carboxy-4-(2-naphthyl)butyrate (10 g, 31.9 mmol) in THF (160 ml) was stirred at −70° C. under argon and lithium bis(trmethylsilyl)amide (63.7 ml of 1M solution in THF, 63.7 mmol) was added dropwise. The mixture was stirred at between −60° C. and −70° C. for 1 hr and then cooled to −80° C. and N-iodosuccinimide (7.17 g, 31.9 mmol) in THF (20 ml) was added via cannula. The mixture was allowed to warm to ~−30° C. over 1 hr and was then quenched with saturated ammonium chloride solution Ethyl acetate was added and the 2-phase mixture was stirred rapidly at room temperature for 1.5 hrs. The layers were separated and the aqueous layer was extracted with ethyl acetate (2×) and the combined organic layers were washed with 5% sodium thiosulfate solution and brine and then dried ($Na_2SO_4$) and evaporated. Chromatography on silica gel (elution with 10% ethyl acetate in hexane) and trituration of the recovered product with hexane gave 5.70 g of a white solid (63%).

MS (AP+ve) M+Na=335 $^1$H NMR ($CDCl_3$): 1.31 (9H, s), 3.29 (1H, dd, J=8.5, 14.6 Hz), 3.38 (1H, dd, J=6.1,14.6 Hz), 4.06 (1H, m), 4.45 (1H, d, J=4.4 Hz), 7.34 (1H, dd, J=1.7, 8.5 Hz), 7.48 (2H, m), 7.68 (1H, s), 7.82 (3H, m).

EXAMPLE

N'-[4-(N-Hydroxyamino)-3S-isopropoxy-2R-(2-naphthylmethyl)succinyl]-S-tert-leucine Methylamide a) N'-[4-(t-Butoxy)-3S-hydroxy-2R-(2-naphthylmethyl)succinyl]-S-tert-leucine Benzyl Ester

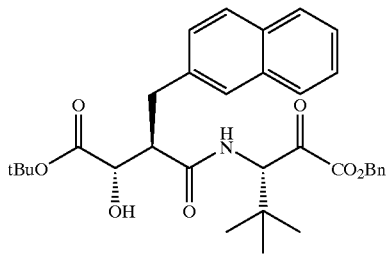

Tert-leucine benzyl ester TFA salt (6.49 g) was stirred with anhydrous potassium carbonate (2.89 g) in THF (100 mL) for 20 min. HOAT (2.24 g) and 3S-t-butoxy-carbonyl-2R-(2-naphthylmethyl)propiolactone (4.66 g, 14.94 mmol) were added and the mixture was stirred for a further 72 hr (additional HOAT (1.02 g) was added after 48 hr). The solids were filtered, and washed well with THF. The combined filtrates were evaporated to a foam which was dissolved in EtOAc and washed with 0.5M HCl, sat. aq. NaHCO$_3$ (2×), water and brine; dried (MgSO$_4$) and evaporated to a gum which was crystallised from hexane/Et$_2$O to give the product as a white solid 6.35 g (80%).

$^1$H NMR (DMSO-d$_6$): 0.88 (9H, s), 1.40 (9H, s), 2.88 (1H, dd, J=13.5, 6 Hz), 3.00 (1H, dd, J=13.5, 8.5 Hz), 3.19 (1H, m), 3.92 (1H, t, J=6.5 Hz), 4.18 (1H, d, J=8.5 Hz), (1H, d, J=12.5 Hz), 4.84 (1H, d, J=12.5 Hz), 5.53 (1H, d, J=7.5), 7.24 (2H 7.37 (4H, m), 7.45 (2H, m), 7.65 (1H, s), 7.77–7.87 (3H, m), 8.09 (1H, d, J≈9 Hz).

b) N'-[4-(t-Butoxy)-3S-isopropoxy-2R-(2-naphthyimethyl)succinyl]-S-tert-leucine Benzyl Ester

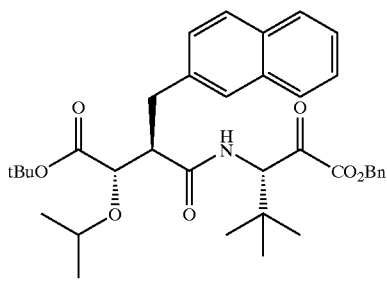

To a solution of N'-[4-(t-butoxy)-3S-hydroxy-2R-(2-naphthylmethyl)succinyl]-S-tert-leucine benzyl ester (3.0 g, 5.62 mmol), in 1,2-diethoxyethane (75 mL) was added NaH (60% suspension in paraffin; 0.27 g), after stirring for 2–3 min., a solution of $^i$PrOTf in pentane (~30% w/w; 6 mL) was added. The mixture was stirred for 25 min. at RT and further NaH (0.054 g) and $^i$PrOTf solution (3 mL) were added. After stirring for a further 25 min., an additional charge of both NaH (0.054 g) and of iPrOTf (3 mL), was added. After stirring for another 20 min., 0.5 M HCl was added, and the mixture was extracted (2×) with EtOAc. The combined extracts were washed with sat. aq. NaHCO$_3$, water and brine; dried (MgSO$_4$) and evaporated to a gum, which was purified by chromatography on silica (hexane/Et$_2$O), giving the product as an almost colourless gum, 1.33 g (41%). MS (ES+ve) M+H=576, M+Na=598.

$^1$H NMR (CDCl$_3$): 0.87 (9H, s), 1.09 (3H, d, J=6.0 Hz), 1.21 (3H, d, J=6.0 (9H, s), 2.87–3.00 (2H, m), 3.10–3.22 (1H, m), 3.69 (1H, 7-tet, J=6.0 Hz), 4.00 (1H, d, J=6.5 Hz), 4.36 (1H, d, J=9 Hz), 4.57 (1H, d, apparent J=12.5 Hz), 4.63 (1H, d, apparent J=12.5 Hz) (two halves of Abq), 6.50 (1H, d, J=9 Hz), 7.15–7.19 (2H, m), 7.27–7.40 (4H, m), 7.40–7.45 (2H, m), 7.60 (1H, s), 7.72–7.80 (3H, m).

c) N'-[4-(t-Butoxy)-3S-isopropoxy-2R-(2-naphthylmethyl)suceinyl]-S-tert-leucine

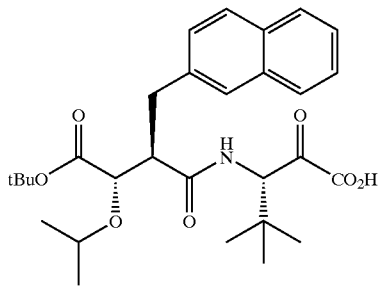

N'-[4-(t-butoxy)-3S-isopropoxy-2R-(2-naphthylmethyl)succinyl]-S-tert-leucine benzyl ester (1.33 g, 2.31 mmol) was hydrogenated at atmospheric pressure in MeOH (38 mL), with Pd—BaSO$_4$ catalyst (0.67 g) for 1 hr. The catalyst was filtered off and washed well with MeOH. The combined filtrates were evaporated to give the product as a foam, 1.09 g (97%).

MS (ES+ve) M+H=486, M+Na=508. $^1$H NMR (DMSO-d$_6$): 0.92 (9H, s), 1.02 (3H, d, J=6.0 Hz), 1.08 (3H, d, J=6.0 Hz), 1,42 (9H, s), 2:75 (1H, dd, J=14,4 Hz), 3.00 (1H, dd, J=14, 9.5 Hz), 3.21 (1H, m), 3.57, (1H, 7-tet, J=6.0 Hz), 3.93 (1H, d, J=8.5 Hz), 4.10 (1H, d, J=9 Hz), 7.29 (1H, m), 2H, m), 7.62 (1H, s), 7.74–7.84 (3H, m), 7.90 (1H, d, J≈9 Hz), 12.35 (1H, v. br.).

d) N'-[4-(t-Butoxy)-3S-isopropoxy-2R-(2-naphthylmethyl)succinyl]-S-tert-leucine Methylamide

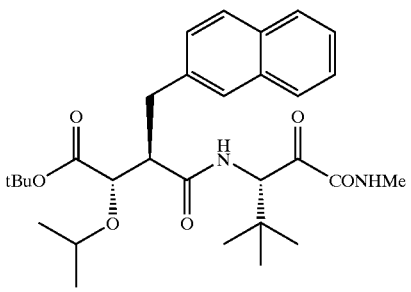

N'-[4-(t-butoxy)-3S-isopropoxy-2R-(2-naphthylmethyl) succinyl]-S-tert-leucine (1.09 g, 2.24 mmol) was dissolved in DMF (29 mL) and treated with HOAT (0.61 g) and DEC (0.86 g). The mixture was stirred at room temp. for 20 min. and methylamine hydrochloride (0.61 g) and N-methylmorpholine (0.74 mL) were then added. The mixture was stirred for a further 2hr. and was then concentrated in vacuo. The residue was dissolved in EtOAc and washed successively with 0.5 M HCl, sat. aq. NaHCO$_3$, water and brine; dried (MgSO$_4$) and evaporated to a gum which was purified by chromatography on silica (hexane/EtOAc). The product was obtained as a gum 0.77 g (69%).

MS (ES+ve) M+H=499, M+Na=521. $^1$H NMR (DMSO-d$_6$): 0.84 (9H, s), 1.02 (3H, d, J=6.0 Hz), 1.09 (3H, d, J=6.0 Hz), 1.45 (9H, s), 2.16 (3H, d, J=4.5 Hz), 2.74 (1H, dd, J=13.5, 4.5 Hz), 2.93 (1H, dd, J=13.5, 10 Hz), 3.17 (1H, m), 3.56 (1H, 7-tet, J=6 Hz), 3.94 (1H, d, J=8.5 Hz), 4.06 (1H, d, J=9.5 Hz), 7.25 (1H, br. m), 7.28 (1H, dd, J=8.5, 1.5 Hz), 7.44 (2H, m), 7.59 (1H, m), 7.67 (1H, d, J=8.5 Hz), 7.74–7.86 (3H, m).

e) N'-[4-Hydroxy-3S-isopropoxy-2R-(2-naphthylmethyl)succinyl]-S-tert-leucine Methylamide

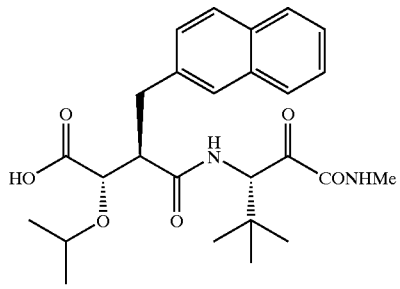

N'-[4-(t-butoxy)-3S-isopropoxy-2R-(2-naphthylmnethyl)succinyl]-S-tert-leucine methylamide (0.77 g, 1.544 mmol), was dissolved in TFA (11 mL) and DCM (22 mL) and stirred at room temp. for 2.5 hr. The solution was evaporated in vacuo and re-evaporated with toluene. Trituration of the residue with ether/hexane gave the product as an off-white solid, 0.67 g (98%).

MS (ES+ve) M+H=443, M+Na=465. $^1$H NMR (DMSO-d$_6$): 0.85 (9H, s), 1.02 (3H, d, J=6.0 Hz), 1.09 (3H, d, J=6.0 Hz), 2.16 (3H, d, J=4.5 Hz), 2.78 (1H, dd, J=14, 5 Hz), 2.95 (1H, dd, J=14, 10.5 Hz), 3.18 (1H, m), 3.58 (1H, 7-tet, J=6 Hz), 4.00 (1H, d, J=8.5 Hz), 4.05 (1H, d, J=9.5 Hz), 7.20 (1H, q, J=4.5 Hz), 7.29 (1H, dd, J=8.5, 1.5 Hz), 7.42–7.46 (2H, m), 7.59 (1H, d, J=9 Hz), 7.60 (1H, s), 7.74–7.84 (3H, m), 12.87 (1H, br. s).

f) N'-[14-(N-Hydroxyamino)-3S-isopropoxy-2R-(2-naphthylmethyl)succinyl]-S-tert-leucine Methylamide

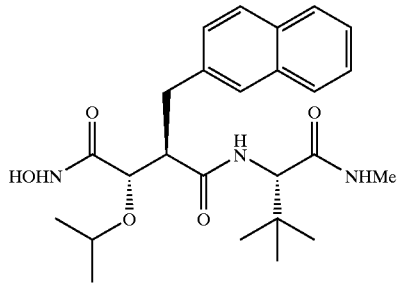

N'-[4-hydroxy-3S-isopropoxy-2R-(2-naphthylmethyl)succinyl]-S-tert-leucine methylamide (0.67 g, 1.514 mmol) was dissolved in DMF (20 mL) and treated with HOAT (0.41 g) and DEC (0.58 g). The solution was stirred at room temp. for 5 min. and hydroxylamine hydrochloride (0.32 g) and N-methylmorpholine (0.5 mL) were added. The mixture was stirred at room temp. for 2 hr, and was then concentrated in vacuo. The residue was partitioned between EtOAc and sat aq. NaHCO$_3$ (2×), water (2×) and brine; dried (MgSO$_4$) and evaporated to a solid which was triturated with ether to give the product as a white solid, 0.51 g (74%).

MS (ES+ve) M+H=458, M+Na=480. $^1$H NMR (DMSO-d$_6$): 0.84 (9H, s), 1.00 (3H, d, J=6.0 Hz), 1.04 (3H, d, J=6.0 Hz), 2.02 (3H, d, J=5 Hz), 2.65 (1H, dd, J=14,4 Hz), 2.83 (1H, dd, J=14, 11.5 Hz), 3.18 (1H, m), 3.52 (1H, 7-tet, J=6.0 Hz), 3.90 (1H, d, J=9 Hz), 4.01 (1H, d, J=9 Hz), 6.93 (1H, q, J=5 Hz), 7.25 (1H, dd, J=8.5, 1.5 Hz), 7.44 (2H, m), 7.53 (1H, d, J=9 Hz), 7.57 (1H, s), 7.75–7.85 (3H, m), 9.08 (1H, s), 10.89 (1H, br. s).

What is claimed is:

1. A compound of formula (I):

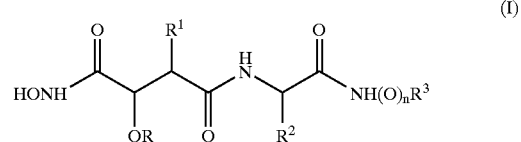

wherein;

R is isopropyl;

n is 0;

R$^1$ is naphthylmethyl;

R$^2$ is t-butyl; and

R$^3$ methyl.

2. A compound according to claim 1 which is a compound of formula (IA):

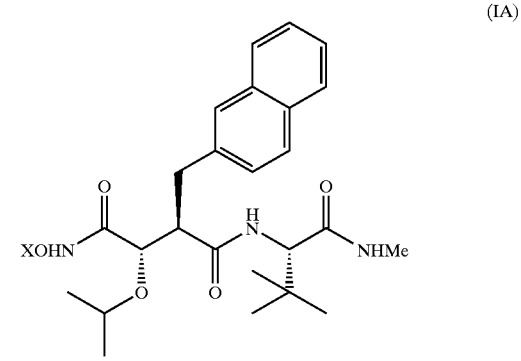

wherein X is a protecting group selected from benzyl and trimethylsilyl.

3. A method for the treatment of a disorder selected from the group consisting of allergy, inflammatory disorders and autoimmune disease in which the overproduction of s-CD23 is implicated, which method comprises the administration of a compound according to claim 1 to a human or non-human mammal in need thereof.

4. A pharmaceutical composition for the treatment of a disorder selected from the group consisting of allergy, inflammatory disorders and autoimmune disease in which the overproduction of s-CD23 is implicated which comprises a compound according to claim 1 and optionally a pharmaceutically acceptable carrier therefor.

5. A process for preparing a compound according to claim 1, which process comprises:

(a) deprotecting a compound of formula (II):

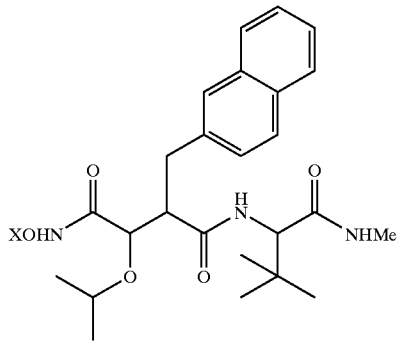

(II)

wherein X is a protecting group selected from benzyl and trimethylsilyl, (b) reacting a compound of formula (III)

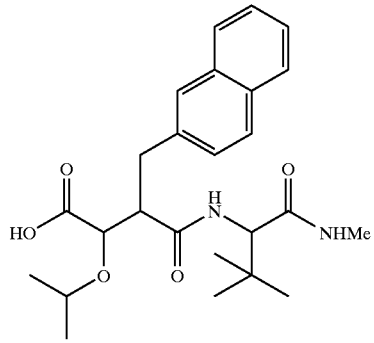

(III)

wherein the hydroxy group is optionally protected, with hydroxylamine or a salt thereof.

6. A compound of formula (II) as defined in claim 5.

7. A compound of formula (III) as defined in claim 5.

8. A method for treating allergic rhinitis or allergic asthma comprising administering to a subject a safe and effective amount of a compound according to claim 1.

* * * * *